United States Patent [19]

Katz

[11] Patent Number: 4,466,438

[45] Date of Patent: Aug. 21, 1984

[54] METHOD AND MEANS FOR TREATING SYMPTOMS OF MENIERE'S DISEASE OR THE LIKE

[76] Inventor: Jay W. Katz, 201 Woodbine Ave., Northport, N.Y. 11768

[21] Appl. No.: 400,155

[22] Filed: Jul. 20, 1982

[51] Int. Cl.$^3$ ............................................. A61F 7/00
[52] U.S. Cl. ................................... 128/400; 128/151; 128/401; 128/742; 128/746; 604/346
[58] Field of Search ................................ 128/399–401, 128/151, 163, 742, 746; 604/346, 355

[56] References Cited

U.S. PATENT DOCUMENTS

| | | | |
|---|---|---|---|
| 1,323,466 | 12/1919 | Gottfried | 128/401 |
| 3,563,231 | 2/1971 | Ducote et al. | 128/733 |
| 3,944,018 | 3/1976 | Satory | 128/151 X |
| 4,023,561 | 5/1977 | Servos | 128/746 X |
| 4,143,649 | 3/1979 | Foti | 128/742 |
| 4,190,033 | 2/1980 | Foti | 128/151 X |
| 4,244,377 | 1/1981 | Grams | 128/401 X |
| 4,299,237 | 11/1981 | Foti | 128/152 X |

Primary Examiner—Kyle L. Howell
Assistant Examiner—Christine A. Fukushima
Attorney, Agent, or Firm—Hopgood, Calimafde, Kalil, Blaustein & Judlowe

[57] ABSTRACT

Binaural thermal-response differentials which are symptomatic of vertigo, particularly Meniere's disease, are treated by establishing a thermal treatment operative via liquid contact with at least one eardrum, thereby establishing a difference in thermal exposure of one ear with respect to the other. Portable apparatus of the invention enables the patient to apply his own therapy whenever he senses onset symptoms of an attack. In certain cases, the apparatus is also useful for prophylactic treatment on an intermittent basis, to foreclose or substantially reduce chances of an attack in periods between treatments.

17 Claims, 6 Drawing Figures

FIG. 4.
FIG. 5.
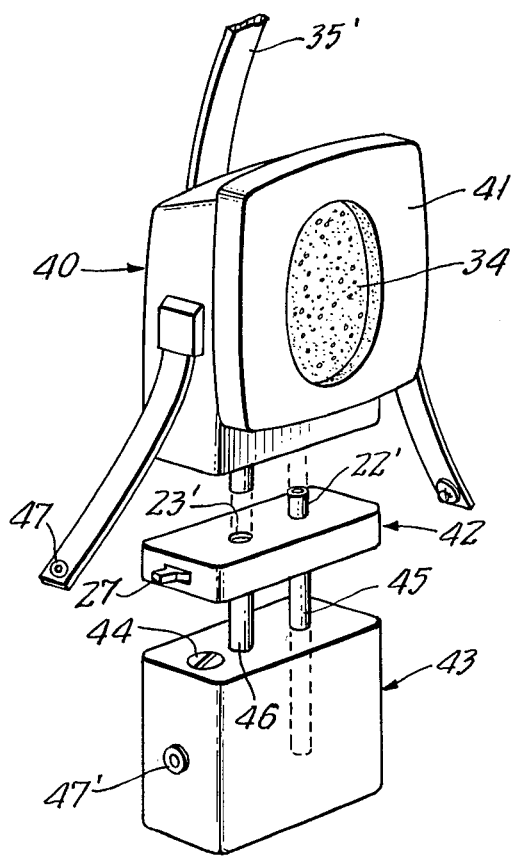
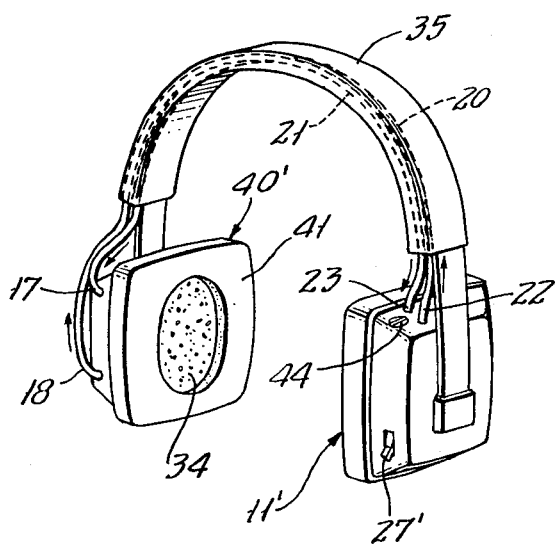
FIG. 6.
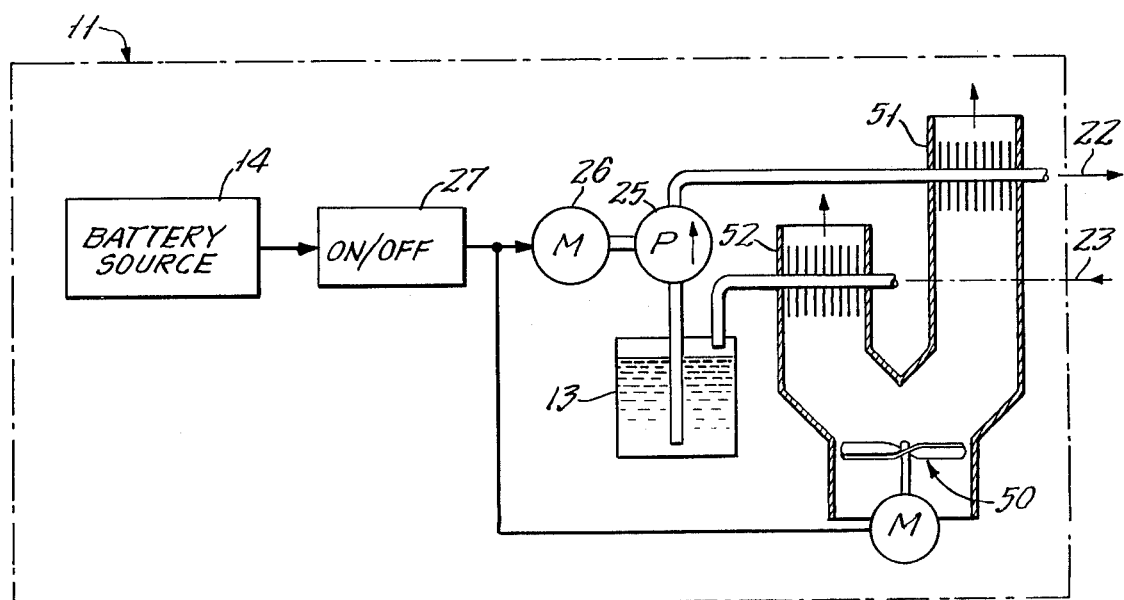

METHOD AND MEANS FOR TREATING SYMPTOMS OF MENIERE'S DISEASE OR THE LIKE

BACKGROUND OF THE INVENTION

The invention pertains to a method for treating a vertigo or the like attack, as when afflicted with Meniere's disease.

My U.S. Pat. No. 4,325,386 describes portable apparatus for treatment of a nystagmus condition in a patient, and said patent contains a substantial background statement which need not now be repeated. The apparatus of said patent deals with controlled supply of gas flow to the region of one or both eardrums, such that a predetermined thermal difference characterizes the environment of the respective ears. Although desirable results are available through use of the patented device, I have found that even more dramatic results are achievable by means other than the gas-flow techniques of said patent; specifically, when the applied thermal environment is via a liquid, a faster result is observed.

BRIEF STATEMENT OF THE INVENTION

It is an object of the invention to provide improved apparatus of the character indicated, whereby caloric irrigation may be available to an afflicted individual for timely, safe and effective treatment of a nystagmus condition.

It is a specific object to provide means whereby a liquid may be the means of caloric irrigation.

Another specific object is to be able to provide the patient with his own portable apparatus, which he may employ for his own liquid-irrigation therapy, either upon his own recognition of the onset of an attack, or in a regular pattern of prophylatic treatments, calculated to forestall likelihood of an attack between treatments.

A further object is to achieve the above objects with apparatus having simplified control means whereby the individual may selectively modify temperature of the irrigating liquid, in accordance with his subjective determination of comfort and dissipation of the attack.

In the forms to be described, the invention achieves the foregoing objects and various further features in the context of caloric-irrigation apparatus wherein the caloric environment is established via a liquid flow, as of water, and wherein the apparatus relies upon a light-weight head-supported concave body which fits to the ear region in the manner of a headphone. The concave body is sufficiently adaptive to the region of an ear so that a closed chamber is established to include the eardrum, and means are provided for circulating-liquid access to the eardrum via the chamber.

DETAILED DESCRIPTION

The invention will be illustratively described for several embodiments, in conjunction with the accompanying drawings, in which:

FIG. 4 is an exploded fragmentary perspective view of another modified embodiment;

FIG. 5 is a perspective view of a further embodiment; and

FIG. 6 is a simplified diagram similar to part of FIG. 1, to show another modification.

Figure 1:
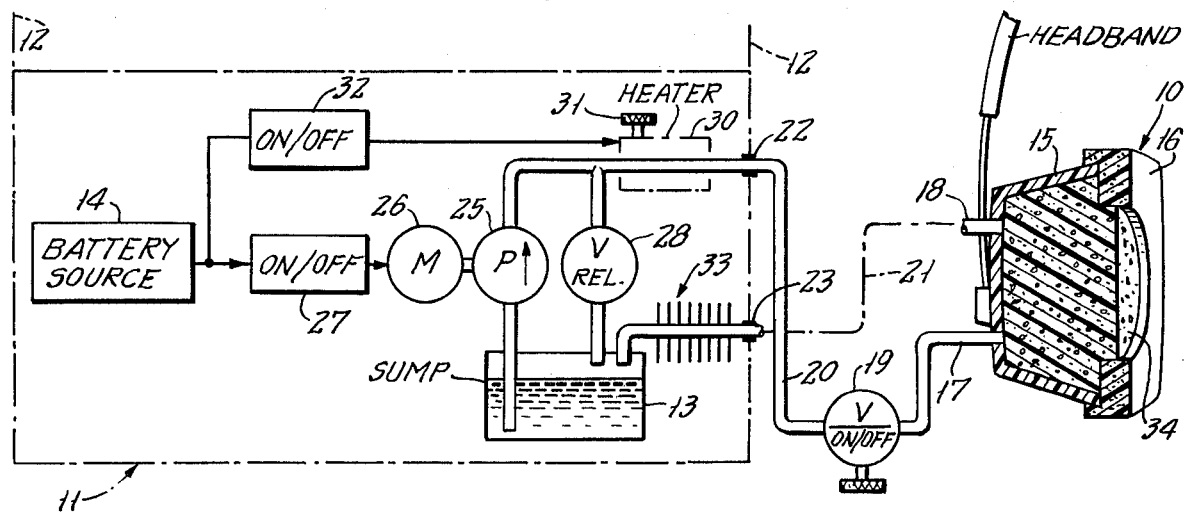
FIG. 1 is a simplified diagram schematically showing components of a presently preferred embodiment of the invention.

The embodiment of FIG. 1 comprises a head-mountable portable unit 10 and a hand or otherwise portable unit 11, which may be shoulder-slung, as suggested by flexible straps 12. Unit 11 is a supply and control casing intended for use to combat an attack. It is equipped with a sump or reservoir 13 for irrigating liquid, such as water, and with a replaceable or rechargeable battery source 14 of electric power.

The head-mounted unit 10 comprises a concave body 15 open at one side for coverage of an ear. It has an annular rim 16 of resiliently compressible material, leaving a central opening whereby the ear (including the eardrum) and the cavity of body 15 define a substantially closed chamber. A suitably compliant arched head band supports body 15 at one end and is in turn referenced to and over the top of the head, in the manner of a telephone headset, with rim 16 resiliently loaded into peripherally sealed contact around the ear. Preferably, rim 16 is a body of air-filled or spongy rubber-like material, with an outer skin, to avoid absorbing irrigating liquid within rim 16. Body 15 is shown with vertically spaced inlet and outlet connections 17–18 and an ON/OFF valve 19 at inlet 17 enables the patient to admit irrigating liquid to the chamber of head unit 10 only when he has adequately mounted the same to his head.

Flexible conduit means, such as first and second lines 20–21 of plastic tubing, connect body inlet 17 with the irrigating-liquid outlet 22 of unit 11, and body outlet 18 with the return-liquid connection 23 of unit 11. In the event of polyethylene or like conduit tubing, valve 19 may be a pinch clamp, and it will be understood that a similar clamp (not shown) may be provided in line 21 near the outlet connection 18, or near connections 22–23, as may be desired.

Within unit 11, a pump 25 is driven by battery-powered motor means 26, under ON/OFF switch control at 27. Pump 25 draws liquid (e.g., water) from sump 13 for delivery via outlet 22 to the chamber at head unit 10, and in the event of a closed condition of valve 19, relief valve means 28 provides a safety-shunt return path to sump 13; the pulsating pump action of commercially available apparatus for dental hygiene (sold under the trademark WATER-PIK) is found to be adequate for purposes herein and to have modest electric-power requirements. Particular treatments may require irrigation at a temperature above or at a temperature below ambient. For elevating the temperature, an electric heater 30 with provisions 31 for selectively variable control of temperature is shown to be operative on pumped liquid delivered to outlet connection 22, depending upon whether a separate ON/OFF switch 32 has been operated. For reducing the temperature of circulation liquid, cooling means is symbolized by radiating fins at 33, operative upon the return line to sump, just after entering unit 11 via connection 23; the symbolism at 33 will be understood to embrace actively aided cooling, as by placement of the finned region in a region of fan-induced draft or of exposure to the cooling effect of carbon dioxide or nitrogen bled from a small replaceable charged bottle (not otherwise shown).

The described structure may be exceedingly compact and of light weight, even with a supply of irrigating liquid at 13 adequate for recirculation throughout a single treatment. The source and control unit 11 will have been charged with irrigation liquid and with battery power, in readiness to meet an attack, once the patient recognizes onset symptoms of a developing nystagmus. The head-mounted unit 10 is as simple to apply as are the headphones of a stereo set; in fact, the unit 10 may completely resemble such a headset. All that is needed, after applying head unit 10, is to turn "ON" switch 27 and to open valve 19. Irrigating liquid then enters the lower region of the chamber of the head unit, rising to flood the ear with direct eardrum contact, before spilling at overflow via outlet 18 and back to sump 13. Cooling or heating of the liquid occurs automatically, as may have been preselected by the physician for accommodation of the patient's particular condition. And preferably, the substantial interior volume of the chamber of body 15 is filled with porous material 34 whereby liquid-sloshing effects are avoided.

The apparatus of FIG. 1 is useful in applications wherein treatment of a single ear evokes a sufficient corrective reaction to restore balance and avoid further development of the attack. In other cases, it is desirable to apply treatment to both ears, and FIGS. 2 and 3 illustrate two versions of such apparatus.

Figure 2:
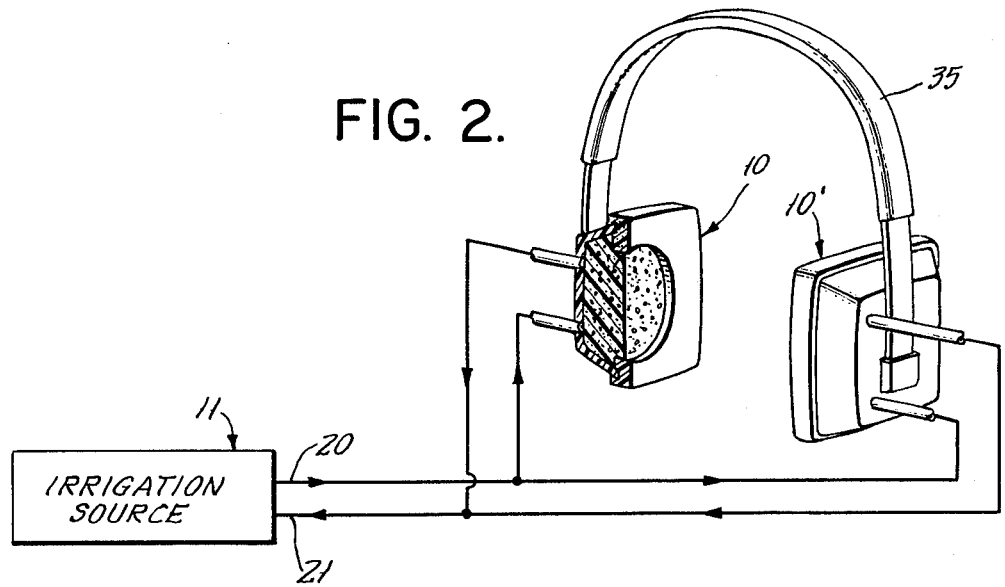
FIGS. 2 and 3 are similar diagrams to schematically show different connections for a modified embodiment.

In FIG. 2, a compliant arcuate headband 35 is connected at opposite ends to separate head units 10—10', which may be duplicates of each other, adapted for substantially sealed irrigation-chamber development at each of the ears of the patient. Outlet and return lines 20-21 from the source unit 11 are connected in parallel to the respective head units 10—10', reliance being placed upon the difference in conduit-line connection to one unit (10) with respect to the other (10') to establish a sufficient difference in irrigation-liquid temperature as delivered to the respective units 10—10', the sufficient difference being polarized as prescribed by the physician for the particular patient.

Figure 3:
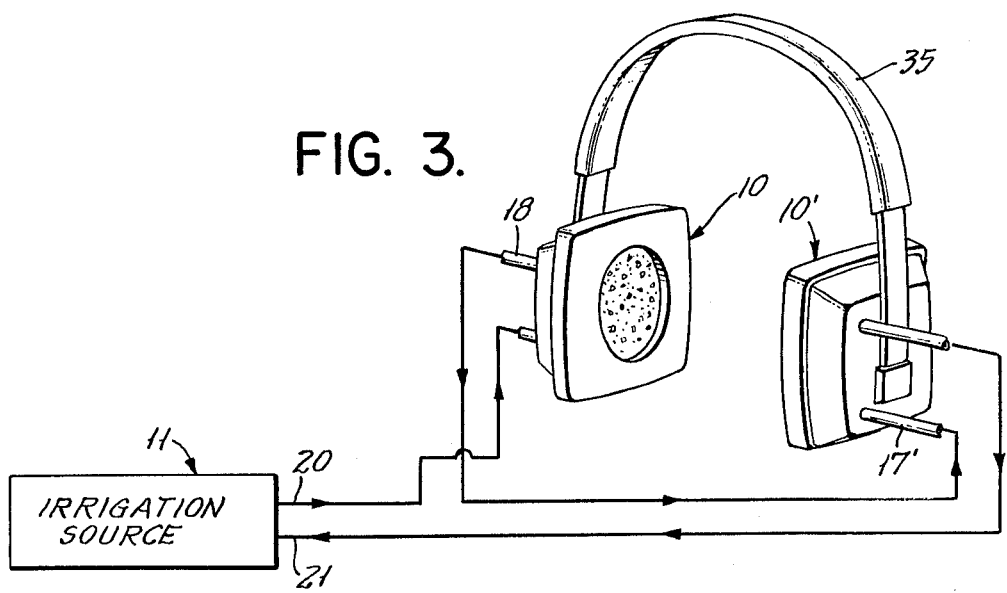

In FIG. 3, the component parts are as decribed for FIG. 2, except that the chambers of the respective head units 10—10' are series-connected to the outlet and return lines 20-21, using a connection line 36 from the outlet 18 of unit 10 to the inlet 17' of unit 10'. In this case, reliance is placed upon body-contact heating of irrigation liquid at unit 10 to sufficiently elevate inlet temperature of liquid entering unit 10' (above the temperature of a liquid entering unit 10) so that therapeutic use may be made of this temperature difference, when the physician precribes the manner of use of the device.

In FIG. 4, the head unit 40 at one end of the headband 35' is of rectangular-prismatic configuration, but otherwise generally in accord with description given for unit 10 in FIG. 1. Thus, soft porous material 34 in the chamber of unit 40 is exposed to the ear within a peripherally continuous seal frame 41 of yieldable non-absorbing construction. A first module 42 will be understood to contain pump, motor and battery components, with severable plug-in adaptability of outlet and return conduit connections 22'-23', sized and spaced for correctly oriented severable connection to the inlet and return-line connections (corresponding to 17-18 of FIG. 1, but not shown in FIG. 4) serving the chamber of head unit 40. A second module 43 will be understood to essentially serve sump or reservoir purposes, being a canteen-like tank with filler closure at 44 and having detachable outlet and return connections 45-46 to module 42, it being understood that aside from the indicated detachable features, the connection of modules 43-42 to unit 40 establishes the functional relation of components described for FIG. 1, the ON/OFF switch 27 function being accessible via an actuating push button 27. It will be understood that use of detachable tank modules as at 43, enables one or more filled spares of such modules to be retained at a desired temperature, e.g., in a refrigerator, in readiness for use as needed. It will be further understood that use of detachable pump modules, as at 42, enables a used spare module 42 to be connected for battery recharging while a freshly charged module 42 is connected to head unit 40 in readiness for use. Snap-button engagement via coacting elements, as at 47—47', provides releasable side-strap retention of modules 42-43 to unit 40.

The description given for FIG. 4 will be understood to be illustrative of a single-ear treatment device (utilizing but a single head unit 40) and of a two-ear treatment device (utilizing separate head units 40) at the respective ends of headband 35'. In the latter event, the cartridge-like character of modules 43 enables the temperature of circulating liquid carried in the module 43 serving one ear to be different from the temperature of circulating other liquid serving the other ear, the temperature difference and its polarity being as may be determined by the prescribing physician to best serve his patient.

The embodiment of FIG. 5 has the appearance and portable convenience of a stereo headset, wherein the irrigating unit 40' at one end of an arcuate headband 35 is generally as described for unit 40, except that the circulating flow of irrigation liquid is via conduit means 20-21 carried by and conforming to the headband 35 and with vertically spaced coupling to chamber inlet and outlet connections 17-18. At the other end of the headband, a source and supply unit 11' may have generally the appearance of unit 40, except that its components will be understood to include the battery operated pump, sump tank with filler cap 44, and outlet and return connections 22-23 to the respective conduit lines 20-21.

FIG. 6 shows a modification of the source and supply unit 11 of FIG. 1, wherein a motor-driven fan 50 is operated in parallel with the pump motor, to establish a driven flow of ambient air in separate ducts 51-52 serving finned regions of the respective outlet and return lines of the liquid-circulation system, thus providing an enhanced degree of cooling action without requiring a charged nitrogen bottle or other repleaceable source of cooling action.

It will be seen that the described invention meets all stated objects with easily applied portable apparatus than can be safely applied by the victim himself, or by whomever happens to be his companion at onset of an attack. The extent to which prescribed apparatus can be simplified (e.g., by providing only for cooling action and/or by presetting of otherwise variable controls) will depend upon the severity of a particular victim's attacks, upon the ability of the victim to correctively and promptly respond to his recognition of onset symptoms of an attack, and upon the interpretative decision of the prescribing physician.

A typical treatment is five minutes with water irrigation in the described structures. Such exposure is found to give prompt and noticeable relief to the victim of an attack, and in prophylactic application, as for such a period each night upon retiring, the treatment is found in certain cases to have caught a developing condition in its incipient stage and to safely forestall any dizziness for the next day. Prophylactic treatment in this manner is effective and beneficial for benign positional vertigo, for labyrinthitis, and for any vestibular dysfunction.

Selection of the ear to be treated will depend on the problem and response of the particular patient, although there is evidence that caloric stimulation of the "wrong" ear can nevertheless effect transfer of a corrective stimulus to the afflicted ear.

While the invention has been described in detail for preferred and illustrative embodiments, it will be understood that modifications may be made without departure from the scope of the invention.

What is claimed is:

1. Portable caloric liquid-flow therapeutic apparatus for treatment of a nystagmus condition in a patient, comprising a first portable unit including a sump, a pump connected for delivery of liquid from said sump to an outlet connection, a power source and selectively operable control means for operating said pump, and a liquid-return connection to said sump; a second portable unit having means for patient-head support at the region of an ear, said second unit comprising a concave body open at one side and adapted for liquid-retaining conformance to the region of the head around the ear, thereby establishing a substantially closed chamber communicating with the eardrum when said body is thus supported, spaced inlet and outlet connections on said body for fluid flow into and out of said chamber, porous means contained by said chamber and interposed between said open side and said inlet and outlet connections; and flexible conduit means separately connecting said pump-outlet connection with said body-inlet connection and said body-outlet connection with said liquid-return connection.

2. The apparatus of claim 1, in which heat-exchange means is associated with one of said connections.

3. The apparatus of claim 1, in which heat-exchange means is associated with at least one of the separate connections of said conduit means.

4. The apparatus of claim 2 or claim 3, in which said heat-exchange means is an electrical heater.

5. The apparatus of claim 2 or claim 3, in which said heat-exchange means includes a radiator exposed to ambient air.

6. The apparatus of claim 1, in which said pump is electric-motor driven and said power source is a battery.

7. The apparatus of claim 1, in which said porous means is a member which is retained in said chamber and which includes a portion interposed between said inlet and outlet connections.

8. The apparatus of claim 7, in which said porous member substantially fills said chamber and is yieldably compressible for local ear profile conformance.

9. The apparatus of claim 1, in which said second portable unit comprises a band adapted to span at least a substantially semicircular extent of the head, with said body connected to and carried at one end of said span.

10. The apparatus of claim 9, in which said first portable unit is connected to and carried at the other end of said span.

11. The apparatus of claim 1, in which said body is one of two in said second portable unit and is adapted for similar conformance to the other ear, said conduit means including further fluid-circulating connections to said second body.

12. The apparatus of claim 11, in which the fluid-circulating connections involving said bodies are in series, whereby a thermal difference may characterize liquid-exposure of one ear in relation to the other ear by reason of sequential contact with the respective ears.

13. The apparatus of claim 11, in which the fluid-circulating connections involving said bodies are in parallel, whereby the thermal property of liquid-exposure to both ears may be substantially the same.

14. The apparatus of claim 11, in which selectively operable valve means is associated with fluid-circulating connections to at least one of said bodies, whereby a predetermined difference in fluid-flow may characterize exposure of the respective ears.

15. Portable caloric liquid-flow therapeutic apparatus for treatment of a nystagmus condition in a patient, comprising a concave body open at one side and adapted for liquid-retaining conformance to the region of the head around the ear, means associated with said body for patient-head support of said body at said region, thereby establishing a substantially closed chamber communication with the inner ear, spaced inlet and outlet connections on said body for fluid flow into and out of said chamber, porous means contained by said chamber and interposed between said open side and said inlet and outlet connections, a sump for containing a supply of liquid, and means including a pump in a liquid-circulating circuit with said inlet and outlet connections and with said sump.

16. The apparatus of claim 15, in which said sump and pump are directly associated and carried with said body.

17. The apparatus of claim 16, in which said sump is selectively detachable from said body connections and is adapted to contain a fresh supply of liquid, whereby the termal state of said sump and its liquid contents may be preconditioned for instant availability of desired circulating-fluid temperature upon attachment to said body connections.

* * * * *